(12) United States Patent
Choi et al.

(10) Patent No.: US 11,250,940 B2
(45) Date of Patent: Feb. 15, 2022

(54) EXERCISE FEEDBACK PROVISION APPARATUS AND METHOD

(71) Applicant: SAMSUNG ELECTRONICS CO., LTD., Suwon-si (KR)

(72) Inventors: Changmok Choi, Seongnam-si (KR); Ui Kun Kwon, Hwaseong-si (KR); Jaechun Lee, Seoul (KR); Jongwook Lee, Seongnam-si (KR); Ha-Neul Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 243 days.

(21) Appl. No.: 16/702,619

(22) Filed: Dec. 4, 2019

(65) Prior Publication Data

US 2020/0107773 A1 Apr. 9, 2020

Related U.S. Application Data

(63) Continuation of application No. 15/659,249, filed on Jul. 25, 2017, now Pat. No. 10,524,729, which is a
(Continued)

(30) Foreign Application Priority Data

Oct. 16, 2014 (KR) ........................ 10-2014-0139667

(51) Int. Cl.
*G16H 20/30* (2018.01)
*A61B 5/11* (2006.01)
(Continued)

(52) U.S. Cl.
CPC ........... *G16H 20/30* (2018.01); *A61B 5/0205* (2013.01); *A61B 5/1118* (2013.01); *A61B 5/486* (2013.01);
(Continued)

(58) Field of Classification Search
CPC .. G16H 20/30; H04M 1/72412; A61B 5/1118; A61B 5/0205; A61B 5/486;
(Continued)

(56) References Cited

U.S. PATENT DOCUMENTS 6,024,575 A 2/2000 Ulrich
2008/0319279 A1* 12/2008 Ramsay ................. A61B 5/486
600/301
(Continued)

FOREIGN PATENT DOCUMENTS

CN 103054585 A 4/2013
CN 103127665 A 6/2013
(Continued)

OTHER PUBLICATIONS

"Pattern." Merriam-Webster.com Dictionary, Merriam-Webster, https://www.merriam-webster.com/dictionary/pattern. Accessed Nov. 18, 2021. (Year: 2021).*
(Continued)

*Primary Examiner* — Sundhara M Ganesan
(74) *Attorney, Agent, or Firm* — NSIP Law (57) ABSTRACT

An exercise feedback provision apparatus includes an acquirer configured to acquire exercise intensity information including either one or both of user biometric information and user movement information, and a controller configured to verify whether the exercise intensity information is in a predetermined range, and generate a control signal based on a result of the verifying. The apparatus further includes a feedback provider configured to output a tactile feedback based on a pattern corresponding to the control signal.

19 Claims, 8 Drawing Sheets

Related U.S. Application Data continuation of application No. 14/672,838, filed on Mar. 30, 2015, now Pat. No. 9,743,883.

(51) Int. Cl.
| | | |
|---|---|---|
| *H04M 1/72412* | (2021.01) | |
| *A61B 5/0205* | (2006.01) | |
| *A61B 5/00* | (2006.01) | |
| *A61B 5/024* | (2006.01) | |
| *A63B 24/00* | (2006.01) | |

(52) U.S. Cl.
CPC ............ *A61B 5/742* (2013.01); *A61B 5/7405* (2013.01); *A61B 5/7455* (2013.01); *A61B 5/7475* (2013.01); *A63B 24/0075* (2013.01); *H04M 1/72412* (2021.01); *A61B 5/02438* (2013.01); *A61B 5/681* (2013.01); *A61B 2503/10* (2013.01); *A63B 2024/0065* (2013.01); *A63B 2024/0068* (2013.01)

(58) Field of Classification Search
CPC ..... A61B 5/7405; A61B 5/742; A61B 5/7455; A61B 5/7475; A61B 5/02438; A61B 2503/10; A61B 5/681; A63B 24/0075; A63B 2024/0065; A63B 2024/0068
See application file for complete search history.

(56) References Cited

U.S. PATENT DOCUMENTS

| | | | |
|---|---|---|---|
| 2009/0177097 A1* | 7/2009 | Ma ..................... | A61B 5/14551 |
| | | | 600/500 |
| 2010/0075806 A1 | 3/2010 | Montgomery | |
| 2010/0027361 A1 | 10/2010 | Johnson | |
| 2012/0225412 A1 | 9/2012 | Wagner | |
| 2012/0238832 A1 | 9/2012 | Jang et al. | |
| 2013/0178335 A1 | 7/2013 | Lin et al. | |
| 2014/0077945 A1 | 3/2014 | Amagai | |
| 2014/0135960 A1 | 5/2014 | Choi | |
| 2014/0278220 A1 | 9/2014 | Yuen | |
| 2015/0099991 A1* | 4/2015 | Yamaguchi .......... | A61B 5/7282 |
| | | | 600/508 |
| 2015/0328081 A1 | 11/2015 | Goldenberg et al. | |
| 2016/0148531 A1* | 5/2016 | Bleich ................. | A61B 5/0205 |
| | | | 434/247 |
| 2016/0256082 A1* | 9/2016 | Ely ....................... | A61B 5/1123 |
| 2017/0014068 A1* | 1/2017 | Gotoh .................. | A61B 5/1118 |
| 2017/0273612 A1* | 9/2017 | Kim ...................... | G06Q 50/01 |

FOREIGN PATENT DOCUMENTS

| | | |
|---|---|---|
| CN | 103226799 A | 7/2013 |
| CN | 103654746 A | 3/2014 |
| EP | 1 512 370 A1 | 3/2005 |
| EP | 1 875 859 A1 | 1/2008 |
| JP | 7-116137 A | 5/1995 |
| JP | 2003-334181 A | 11/2003 |
| JP | 2007-75201 A | 3/2007 |
| JP | 4068965 B2 | 3/2008 |
| JP | 2010-530281 A | 9/2010 |
| JP | 2010-536040 A | 11/2010 |
| JP | 2014-54479 A | 3/2014 |
| JP | 2014-120934 A | 6/2014 |
| KR | 10-0714093 B1 | 5/2007 |
| KR | 10-2013-0016052 A | 2/2013 |
| KR | 10-2013-0042268 A | 4/2013 |
| WO | WO 2005/082471 A1 | 9/2005 |

OTHER PUBLICATIONS

Extended European Search Report dated Mar. 17, 2016 in counterpart European Patent Application No. 15190060.2 (8 pages in English).
European Office Action dated Jul. 27, 2018, in corresponding European Application No. 15 190 060.2 (8 pages, in English).
Chinese Office Action dated Nov. 12, 2018, in corresponding Chinese Application No. 201510346720.8 (17 pages in English, 11 pages in Chinese).
Japanese Office Action dated Apr. 2, 2019 in corresponding Japanese Patent Application No. 2015-148322 (3 pages in English, 5 pages in Japanese).
Korean Office Action dated Jan. 26, 2021 in counterpart Korean Patent Application No. 10-2014-0139667 (5 pages in English, 9 pages in Korean).
Extended European Search Report dated Jul. 30, 2021 in counterpart European Patent Application No. 21169652.1. (13 pages in English).

* cited by examiner

EXERCISE FEEDBACK PROVISION APPARATUS AND METHOD

CROSS-REFERENCE TO RELATED APPLICATION

This application is a continuation of U.S. application Ser. No. 15/659,249 filed on Jul. 25, 2017 which is a continuation of U.S. application Ser. No. 14/672,838 filed on Mar. 30, 2015, now U.S. Pat. No. 9,743,883 issued on Aug. 29, 2017 which claims the benefit under 35 USC 119(a) of Korean Patent Application No. 10-2014-0139667, filed on Oct. 16, 2014, in the Korean Intellectual Property Office, the entire disclosures of which are all incorporated herein by reference for all purposes.

BACKGROUND

1. Field

The following description relates to an exercise feedback provision apparatus and method.

2. Description of Related Art

An improving life standard has brought about an increased level of interest in life-enhancing health management, and thus, a medical service for managing a health status has developed rapidly. Along with an increase in demands on such medical services, an interest in health care combining medical technology and information technology (IT) is also increasing according to IT development. In this context, health care functioning devices are supplied to provide contents of a user such as a step count, calorie consumption, and the like. Recently, active research is being conducted on technology for acquiring a state of health of a user to provide appropriate health information to the user.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an exercise feedback provision apparatus including an exercise feedback provision apparatus including an acquirer configured to acquire exercise intensity information including either one or both of user biometric information and user movement information, and a controller configured to verify whether the exercise intensity information is in a predetermined range, and generate a control signal based on a result of the verifying. The apparatus further includes a feedback provider configured to output a tactile feedback based on a pattern corresponding to the control signal.

The feedback provider may be configured to output a first tactile feedback based on a first pattern in response to the exercise intensity information being greater than the predetermined range, output a second tactile feedback based on a second pattern in response to the exercise intensity information being in the predetermined range, and output a third tactile feedback based on a third pattern in response to the exercise intensity information being less than the predetermined range.

The user biometric information may include a heart rate of a user, and the user movement information may include either one or both of a moving speed and a step count of the user.

The apparatus may further include a communication interface configured to receive the pattern from an external device.

The apparatus may further include a user interface configured to receive a user input for setting the pattern.

The controller may be configured to set the predetermined range based on a heart rate of a user.

The heart rate of the user may include either one or both of a maximum heart rate and a heart rate of an anaerobic exercise threshold of the user.

The feedback provider may be configured to output either one or both of an auditory feedback and a visual feedback based on the pattern.

The controller may be configured to generate the pattern based on a change in the exercise intensity information.

In another general aspect, there is provided an exercise feedback provision apparatus including an acquirer configured to acquire exercise intensity information including either one or both of user biometric information and user movement information, and a feedback provider configured to output a tactile feedback at a reference speed in response to the acquiring. The apparatus further includes a controller configured to verify whether the exercise intensity information is in a predetermined range, and control an output speed of the tactile feedback based on a result of the verifying.

The controller may be configured to change the output speed to differ from the reference speed in response to the exercise intensity information being outside the predetermined range.

The controller may be configured to control the output speed to be lower than the reference speed in response to the exercise intensity information being greater than the predetermined range, and control the output speed to be higher than the reference speed in response to the exercise intensity information being less than the predetermined range.

The controller may be configured to control the output speed based on a change in the exercise intensity information.

The apparatus may further include a user interface configured to receive a user input for setting the output speed.

The apparatus may further include a communication interface configured to receive the output speed from an external device.

In still another general aspect, there is provided an exercise feedback provision method of an exercise feedback provision apparatus, the method including acquiring exercise intensity information including either one or both of user biometric information and user movement information, verifying whether the exercise intensity information is in a predetermined range, generating a control signal based on a result of the verifying, and outputting a tactile feedback based on a pattern corresponding to the control signal.

The outputting may include outputting a first tactile feedback based on a first pattern in response to the exercise intensity information being greater than the predetermined range, outputting a second tactile feedback based on a second pattern in response to the exercise intensity information being in the predetermined range, and outputting a third tactile feedback based on a third pattern in response to the exercise intensity information being less than the predetermined range.

The method may further include receiving the pattern from an external device paired with the exercise feedback provision apparatus.

The method may further include receiving a user input for setting the pattern.

In yet another general aspect, there is provided an exercise feedback provision apparatus including a controller configured to verify whether a user exercise intensity is in a predetermined range, and a feedback provider configured to output a first tactile feedback in response to the user exercise intensity being in the predetermined range, and output a second tactile feedback in response to the user exercise intensity being outside the predetermined range.

The user exercise intensity may include any one or any combination of a heart rate, a moving speed, and a step count of a user.

The first tactile feedback may have either one or both of a pattern and a speed that are different than that of the second tactile feedback.

Other features and aspects will be apparent from the following detailed description, the drawings, and the claims.

DETAILED DESCRIPTION

The following detailed description is provided to assist the reader in gaining a comprehensive understanding of the methods, apparatuses, and/or systems described herein. However, various changes, modifications, and/or equivalents of the methods, apparatuses, and/or methods described herein will be apparent to one of ordinary skill in the art. For example, the sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

An apparatus described below with reference to various examples may be an apparatus for performing a communicational function. As an example, the apparatus may include, for example, a mobile apparatus, a wearable apparatus, a tablet personal computer (PC), and a head mount display apparatus (HMD). Also, it will be apparent, to one of ordinary skilled in the art, that a type of the apparatus is not limited to the foregoing.

Figure 1:
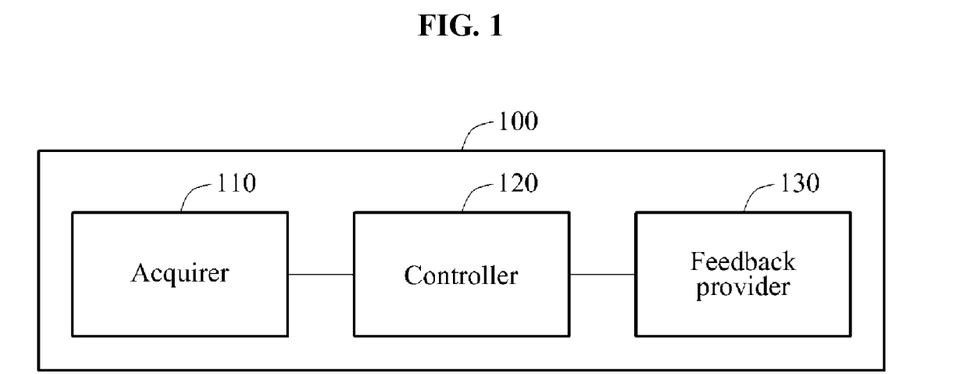
FIG. 1 is a block diagram illustrating an example of an exercise feedback provision apparatus.

FIG. 1 is a block diagram illustrating an example of an exercise feedback provision apparatus 100. Referring to FIG. 1, the exercise feedback provision apparatus 100 includes an acquirer 110, a controller 120, and a feedback provider 130.

The acquirer 110 acquires exercise intensity information of a user. While exercising, the user may be under strain by performing a movement. Exercise intensity may indicate a level of strain affecting a body of the user. The acquirer 110 may acquire information of the body changed due to the strain. As an example, user biometric information including, for example, a heart rate, an oxygen intake, and a maximum oxygen intake of the user may be changed while exercising. Also, user movement information including, for example, a moving speed and a step count of the user may be changed while exercising. The acquirer 100 may acquire user heart rate information, user moving speed information, and user step count information.

The acquirer 110 may acquire the user biometric information, using a heartbeat sensor, for example, a photoplethysmography (PPG). Also, the acquirer 110 may acquire the user movement information, using an acceleration sensor.

The controller 120 verifies whether the acquired exercise intensity information is in a target range, i.e., a predetermined range. The exercise intensity information of the user may change while exercising; for example, the heart rate of the user may increase. Also, the moving speed of the user may increase during the exercise. For example, the controller 120 may verify whether the heart rate or the moving speed of the user is in the target range.

The controller 120 may set the target range based on the heart rate of the user. In this example, the target range may be a range of the heart rate. As an example, the controller 120 may estimate a maximum heart rate of the user based on an age of the user, and set 60% through 70% of the estimated maximum heart rate as the target range. As another example, the controller 120 may verify the maximum heart rate of the user within a predetermined period of time from a point in time at which the user starts the exercise, for example, within five minutes after the user starts exercising. Based on the verified maximum heart rate, the controller 120 may adaptively set the target range. As still another example, the controller 120 may set the target range based on a heart rate of an anaerobic exercise threshold. Using a communication interface, the acquirer 110 may acquire the heart rate of the anaerobic exercise threshold extracted based on a change in an electromyogram (EMG) signal of the user. The exercise feedback provision apparatus 100 may transmit, to a server, a request for the heart rate of the anaerobic exercise threshold of the user, and receive, from the server, the heart rate of the anaerobic exercise threshold of the user. Using the communication interface, the acquirer 110 may also acquire the heart rate of the anaerobic exercise threshold of the user from a device paired with the exercise feedback provision apparatus 100. Alternatively, the acquirer 110 may verify the heart rate of the user by an exercise period expiring, and extract a heart rate corresponding to the anaerobic exercise threshold from the verified heart rate. The controller 120 may determine the extracted heart rate as the heart rate of the anaerobic exercise threshold, and set the target range based on the determined heart rate of the anaerobic exercise threshold.

Based on a result of the verifying of whether the exercise intensity information is in the target range, the controller 120 may generate a control signal. As an example, the controller 120 may generate a first control signal when the acquired exercise intensity information is verified to be greater than the target range. The controller 120 may generate a second control signal when the acquired exercise intensity information is verified to be within the target range. The controller 120 may generate a third control signal when the acquired exercise intensity information is verified to be less than the target range. The controller 120 may generate a diversified control signal such that the user receives various forms of exercise feedback. As another example, the controller 120 may generate a control signal when the acquired exercise intensity information is verified to be within the target range. When the acquired exercise intensity information is verified to be outside the target range, the controller 120 may generate a control signal different from the generated control signal. In either of the aforementioned cases, the controller 120 may generate a diversified control signal such that the user receives various exercise feedbacks.

The feedback provider 130 outputs a tactile feedback based on an output pattern corresponding to the control signal generated by the controller 120. For example, when the acquired exercise intensity information is verified to be greater than the target range, and when the controller 120 generates the first control signal, the feedback provider 130 may drive a vibration motor based on a first output pattern corresponding to the first control signal. In addition, when the acquired exercise intensity information is verified to be within the target range, and when the controller 120 generates the second control signal, the feedback provider 130 may drive the vibration motor based on a second output pattern corresponding to the second control signal. Also, when the acquired exercise intensity information is verified to be less than the target range, and when the controller 120 generates the third control signal, the feedback provider 130 may drive the vibration motor based on a third output pattern corresponding to the third control signal. The feedback provider 130 may output the tactile feedback based on the output pattern corresponding to the control signal generated by the controller 120, thereby providing various exercise feedbacks to the user.

As another example, the controller 120 may divide a range including the exercise intensity information into a target range and a range other than the target range. The controller 120 may generate a control signal when the exercise intensity information is verified to be within the target range, and generate a control signal different from the aforementioned control signal when the exercise intensity information is verified to be outside the target range. In either of the aforementioned cases, the feedback provider 130 may output distinguishable tactile feedbacks.

The exercise feedback provision apparatus 100 may further include a communication interface configured to receive the output pattern from an external device. The communication interface may include, for example, a wireless Internet interface such as a wireless local area network (WLAN), a wireless fidelity (WiFi) direct, a digital living network alliance (DLNA), a wireless broadband (WiBro), a world interoperability for microwave access (WiMAX), and a high speed downlink packet access (HSDPA), and a local communication interface such as a Bluetooth™ module, a radio frequency identification (RFID) tag, an infrared data association (IrDA), an ultra wideband, a ZigBee, and a near field communication (NFC). Also, the communication interface may include any interface, for example, a wired interface, capable of communicating with an external source.

The external device may be a device connected to the exercise feedback provision apparatus 100 using the communication interface. For example, the external device may be a wearable device and/or a mobile terminal paired with the exercise feedback provision apparatus 100.

The external device may set the output pattern of the tactile feedback output from the exercise feedback apparatus 100 based on a user input. For example, the external device may include a touch display, and display a user interface for setting the output pattern on the touch display. The user may apply the input to the user interface displayed on the touch display, and the external device may sense a touch event occurring in response to the input. The external device may set the output pattern in response to the sensing of the touch event.

For example, the external device may display the interface for setting the output pattern corresponding to each of the cases in which the exercise intensity information is greater than the target range, the target range, and less than the target range. That is, based on the input of the user, the external device may set the output pattern corresponding to the case in which the exercise intensity information is greater than the target range, and set the output pattern corresponding to the case in which the exercise intensity information is less than the target range. Also, the external device may set the output pattern corresponding to the case in which the exercise intensity information is in the target range, based on the input of the user.

Concurrently with the setting of the output pattern in the external device, the exercise feedback provision apparatus 100 may output the tactile feedback based on the set output pattern. For example, the user may set a pattern of a vibration output from the wearable device, using the mobile terminal. Concurrently with the setting of the pattern of the vibration, the wearable device paired with the mobile terminal may output the vibration based on the set pattern. The user may verify the pattern of the vibration set by the user, and modify the pattern of the vibration using the mobile terminal.

The exercise feedback provision apparatus 100 may further include a user interface configured to receive a selection input for setting the output pattern from the user. For example, the exercise feedback provision apparatus 100 may include a touch display to receive a touch input from the user. Based on the touch input of the user, the exercise feedback provision apparatus 100 may set the output pattern of the tactile feedback.

The controller 120 may adaptively generate an additional output pattern based on the acquired exercise intensity information. For example, a heart rate corresponding to the target range may be "100" through "120". When a heart rate of a user doing exercise is "130", the controller 120 may verify that the heart rate of the user is greater than the target range, and output the tactile feedback based on the output pattern corresponding to the result of the verifying. In this example, the user may not decrease a running speed despite an output of the tactile feedback. The controller 120 may sense that the exercise intensity information is not changed, and adaptively generate the additional output pattern based on a result of the sensing. Based on the additional output pattern, the feedback provider 130 may additionally output a tactile feedback, a visual feedback, and an auditory feedback such that the user decreases the running speed in response to the additional outputting.

As another example, when the user increases the running speed although the heart rate of the user is greater than the target range, the controller 120 may sense that the exercise intensity information is not changed in a desired direction. The controller 120 may adaptively generate the additional output pattern indicating the user is to decrease the running speed. The feedback provider 130 may additionally output the tactile feedback, the visual feedback, and the auditory feedback based on the additional output pattern.

The feedback provider 130 may output at least one of the visual feedback and the auditory feedback based on the output pattern. The exercise feedback provision apparatus 100 may include a display and a light-emitting diode (LED). The LED may emit lights based on the output pattern. Also, a message indicating the user is to increase a speed may be displayed on the display, and an alarming sound may be output.

The controller 120 may sense a user manipulation corresponding to a suspension of outputting the tactile feedback. For example, the controller 120 may sense an action of the user covering the exercise feedback provision apparatus 100, using a hand. In response to the sensing, the controller 120 may suspend the outputting of the tactile feedback. Also, the controller 120 may sense at least one of a change in a contact resistance between the exercise feedback provision apparatus 100 and the user, and a change in a contact level between the exercise feedback provision apparatus 100 and the user. The controller 120 may suspend the outputting of the tactile feedback in response to the sensing.

Figure 2:
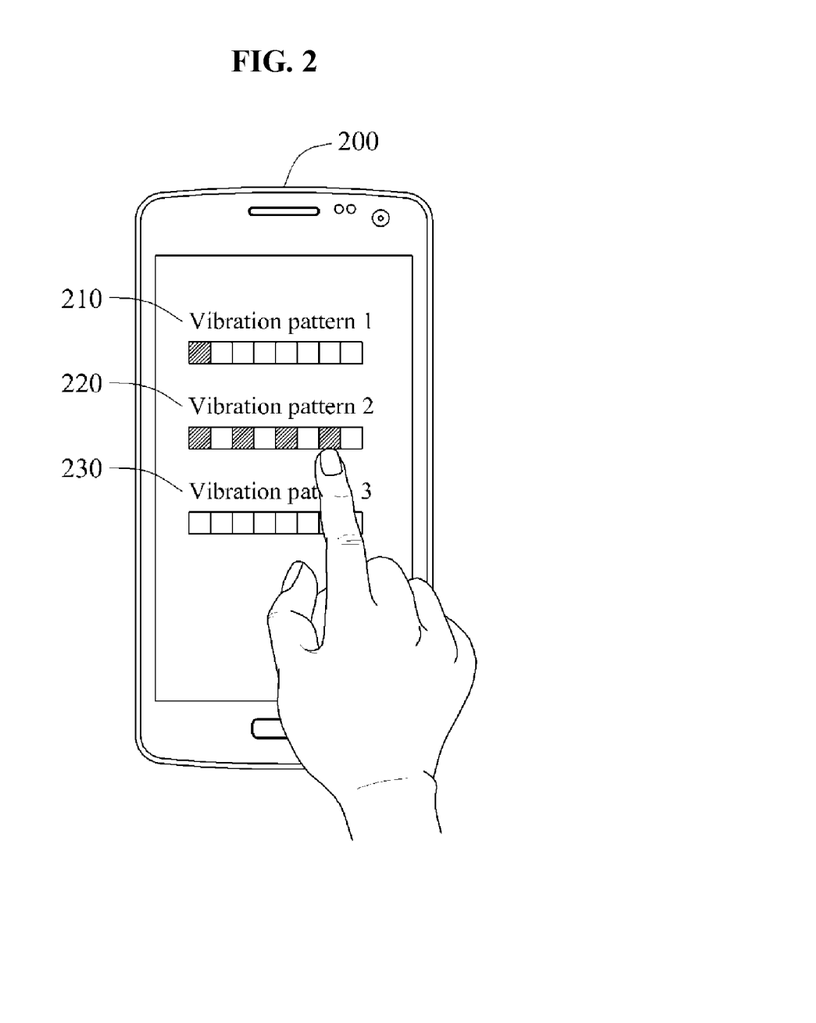
FIGS. 2 and 3 are diagram illustrating examples of a pattern of an exercise feedback.
Figure 3:
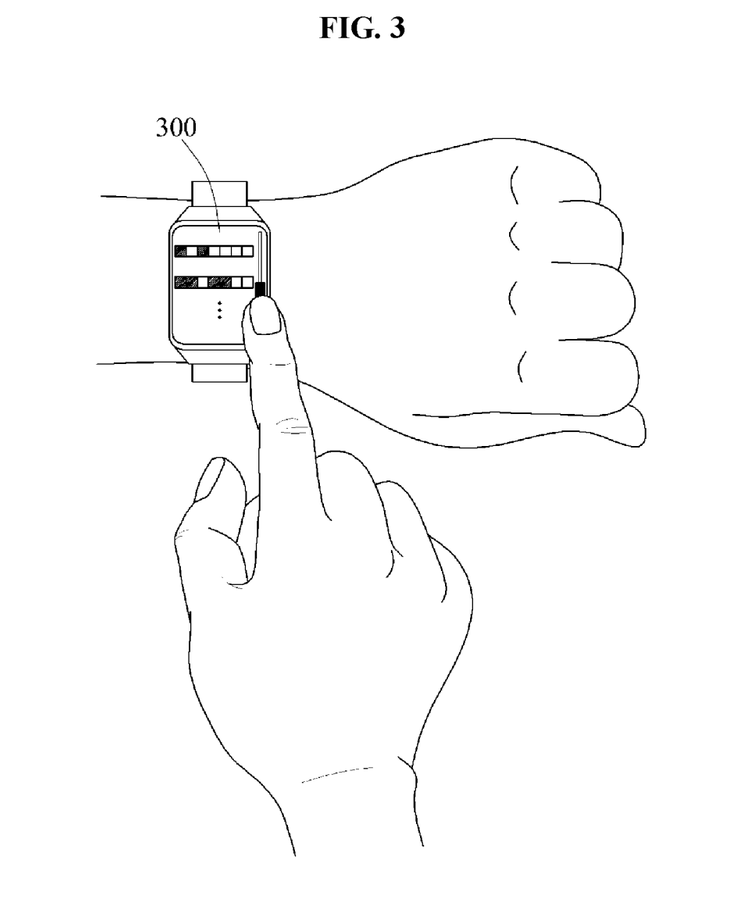

FIGS. 2 and 3 are diagrams illustrating examples of a pattern of an exercise feedback.

Referring to FIG. 2, a user may set a pattern of an exercise feedback, using a mobile terminal 200. An exercise feedback provision apparatus may receive the set pattern, using a communication interface. When a predetermined condition is satisfied, the exercise feedback provision apparatus may provide the exercise feedback based on the pattern.

When exercise intensity information including at least one of user biometric information and user movement information is beyond a target range, a pattern corresponding to a case in which the exercise intensity information is greater than the target range, and a pattern corresponding to a case in which the exercise intensity information is less than the target range, may be set. In this example, the target range may correspond to an optimal exercise intensity of the user. The user may efficiently do an exercise at the optimal exercise intensity. For example, the target range may be a range of a target heart rate set based on a heartbeat of the user. Alternatively, the target range may be a range of a moving speed corresponding to the range of the target heart rate of the user.

The moving terminal 200 displays a user interface for setting a vibration pattern 1 210, a vibration pattern 2 220, and a vibration pattern 3 230.

In FIG. 2, the vibration pattern 1 210 may be an exercise feedback corresponding to the case in which the exercise intensity information of the user is greater than the target range. The vibration pattern 1 210 is "10000000". When the vibration pattern 1 210 is output from the exercise feedback provision apparatus, the user may decrease the moving speed such that the exercise intensity information is within the target range.

The vibration pattern 2 220 may be an exercise feedback corresponding to the case in which the exercise intensity information of the user is less than the target range. The vibration pattern 2 220 is "10101010". When the vibration pattern 2 220 is output from the exercise feedback provision apparatus, the user may increase the moving speed such that the exercise intensity information is within the target range.

The vibration pattern 3 230 may be an exercise feedback corresponding to the case in which the exercise intensity information of the user is within the target range. The vibration pattern 3 230 is "00000000". When the heart rate or a running speed of the user is within the target range, the exercise feedback provision apparatus does not provide the exercise feedback. Alternatively, the vibration pattern 3 230 may be set as "11111111". When the vibration pattern 3 230 is set as "11111111", and when the exercise intensity information of the user is within the target range, an output of a tactile feedback may be performed continuously. When the tactile feedback is continuously output, the user may pay attention to the tactile feedback during the exercise. The user may apply an input to the exercise feedback provision apparatus such that a set value of the vibration pattern 3 230 is changed. The user may perform a motion of covering the exercise feedback provision apparatus, using a hand during a predetermined period of time. Through this, the exercise feedback provision apparatus may sense the motion of the user. In response to the sensing, the exercise feedback provision apparatus may change the set value of the vibration pattern 3 230. The exercise feedback provision apparatus may output the tactile feedback based on the changed set value.

The setting of the pattern for the exercise feedback may include setting an output speed of the tactile feedback. Alternatively or additionally, the setting of the pattern for the exercise feedback may include setting an output period of the tactile feedback. When the output pattern of the tactile pattern is set as the vibration pattern 1 210, the output speed of the tactile feedback may be relatively low, and the output period of the tactile feedback may be relatively long. When the output pattern of the tactile feedback is set as the vibration pattern 2 220, the output speed of the tactile feedback may be relatively high, and the output period of the tactile feedback may be relatively short.

When the exercise intensity information of the user is greater than the target range, the exercise feedback provision apparatus may prolong the output period of the tactile feedback. When the exercise intensity information of the user is less than the target range, the exercise feedback provision apparatus may shorten the output period of the tactile feedback. When the exercise intensity information of the user is within the target range, the exercise feedback provision apparatus may disallow the tactile feedback to be output.

In an example, the mobile terminal 200 may output a message indicating the user may apply an input during a predetermined period of time, for example, for ten seconds. The user may apply a touch input on the display during the predetermined period of time. In response to the applying, the mobile terminal 200 may sense an electrical signal, and set a vibration pattern such that the electrical signal corresponds to the vibration pattern or the output pattern of the tactile feedback. For example, the user may arbitrarily apply the touch input to the mobile terminal 200 to set the output pattern. The mobile terminal 200 may sense an electrical signal corresponding to the touch input applied arbitrarily, and set a vibration pattern based on the electrical signal. The exercise feedback provision apparatus may provide a tactile feedback based on the vibration pattern or an output pattern corresponding to the touch input arbitrarily applied by the user.

Referring to FIG. 3, a user wears an exercise feedback provision apparatus 300 provided in a form of a wearable device. The user sets an output pattern of a tactile feedback in the exercise feedback provision apparatus 300.

In the exercise feedback provision apparatus 300, a display displays a plurality of output patterns. The user may scroll up and down to select an output pattern from the plurality of output patterns. Based on a selection input of the user, the exercise feedback provision apparatus 300 sets the output pattern.

The exercise feedback provision apparatus 300 displays a user interface on the display, and sets the output pattern based on an input for the user interface. As described with reference to FIG. 3, the exercise feedback provision apparatus 300 provides a list of preset vibration patterns. Also, the exercise feedback provision apparatus 300 displays the user interface on the display such that the user sets the output pattern.

As an example, the exercise feedback provision apparatus 300 sequentially displays a plurality of blocks on the display. The user may select a block from the blocks, and the exercise feedback provision apparatus 300 may change a graphics property of the selected block. For example, the exercise feedback provision apparatus 300 may change a color of the selected block. The block of which the graphics property is changed may correspond to an output of the tactile feedback. Also, the user may set an output intensity of the tactile feedback by selecting the block. The exercise feedback provision apparatus may sense a period of time of the user touching the block, and match the period and the output intensity of the tactile feedback. The exercise feedback provision apparatus 300 may match a case in which the period of time of the user touching the block is relatively long and a case in which the output intensity is relatively high.

In an example, the exercise feedback provision apparatus 300 may output a message indicating the user is to touch the display to set the output pattern. The user may apply a touch input to the display during a predetermined period of time, for example, ten seconds. The exercise feedback provision apparatus 300 may sense an electrical signal generated in response to the touch input, and set the output pattern such that the tactile feedback is output based on the electrical signal. For example, when an electrical signal "110011001100" is generated in response to the touch input of the user, the exercise feedback provision apparatus may set the output pattern such that the tactile feedback is provided based on the electrical signal "110011001100". An input pattern of the user may correspond to the output pattern of the tactile feedback.

In an example, the exercise feedback provision apparatus 300 may recognize a step of the user using an acceleration sensor, and coach the user for an exercise speed, using a vibration feedback. Also, the exercise feedback provision apparatus 300 may output a message indicating the user is to take a step for each vibration time. For example, when a speed of taking a step is two beats per minute (bpm), and when a running speed is to be reduced due to a heart rate higher than a target heart rate, the exercise feedback provision apparatus 300 may output a vibration at an interval of 1.5 bpm, and send a feedback indicating the user is to keep pace with the output vibration such that the user reduces the running speed.

Figure 4:
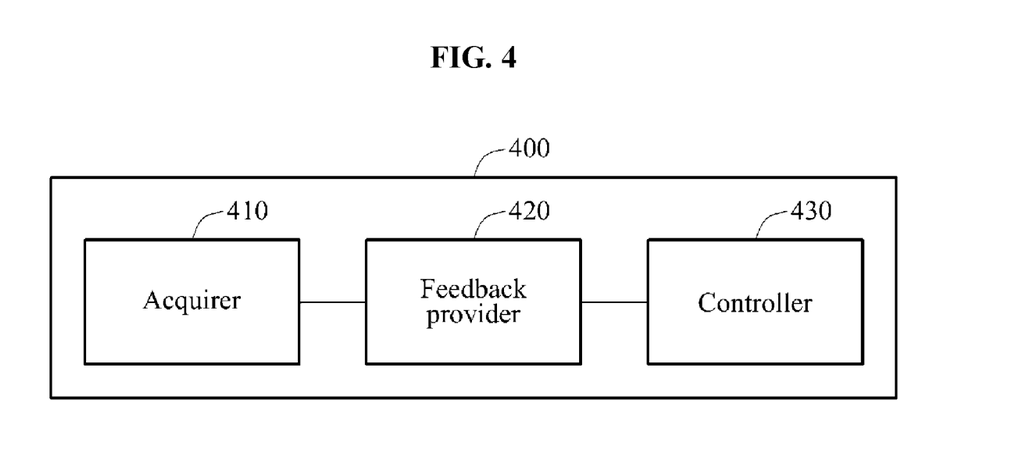
FIG. 4 is a block diagram illustrating another example of an exercise feedback provision apparatus.

FIG. 4 is a block diagram illustrating another example of an exercise feedback provision apparatus 400. Referring to FIG. 4, the exercise feedback provision apparatus 400 includes an acquirer 410, a feedback provider 420, and a controller 430.

The acquirer 410 acquires exercise intensity information including at least one of user biometric information and user movement information. From a user, the acquirer 410 may acquire at least one of heart rate information, maximum heart rate information, and information of a heart rate of an anaerobic oxygen threshold. Also, the acquirer 410 may acquire, from the user, at least one of moving distance information, moving speed information, and step count information.

The feedback provider 420 outputs a tactile feedback at a reference speed in response to the acquiring of the exercise intensity information. When an exercise application stored in the exercise feedback provision apparatus 400 is executed, the feedback provider 420 may output the tactile feedback at the reference speed. For example, the feedback provider 420 may drive a vibration motor such that a vibration is output at a speed of 60 bpm.

The controller 430 verifies whether the exercise intensity information is in one of the target range, a range greater than the target range, and a range less than the target range. The target range corresponds to an optimal exercise intensity of the user. The target range may be a range of a target heart rate that is set based on a heart rate of the user. Alternatively, the target range may be a range of a moving speed corresponding to the range of the target heart rate of the user.

As an example, the controller 430 may verify whether a heartbeat of the user is in a range greater than the target heart rate, the range of the target heart rate, or a range less than the target heart range. As another example, the controller 430 may verify whether the heartbeat of the user is in the range of the target heart rate or in a range other than the range of the target heart rate.

The controller 430 controls an output speed of the tactile feedback based on a result of the verifying. In a state in which the tactile feedback is being output at the reference speed, the controller 430 controls the output speed of the tactile feedback.

As an example, when the exercise intensity information of the user is in the range greater than the target range, the controller 430 may generate a control signal to reduce the output speed of the tactile feedback. That is, when the exercise intensity information on the user is in the range greater than the target range, the controller 430 may control the output speed such that the tactile feedback is output at a speed lower than the reference speed. The feedback provider 420 may output the tactile feedback at a speed of 59 bpm, which is lower than the speed of 60 bpm. When the exercise intensity information on the user is in the range less than the target range, the controller 430 may generate a control signal to increase the output speed of the tactile feedback. That is, when the exercise intensity information on the user is in the range less than the target range, the controller 430 may control the output speed such that the tactile feedback is output at a speed higher than the reference speed. The feedback provider 420 may output the tactile feedback at a speed of 61 bpm, which is higher than the speed of 60 bpm. When the exercise intensity information on the user is in the target range, the controller 430 may control the output speed such that the tactile feedback is output at the reference speed.

As another example, when the exercise intensity information is in the range other than the target range, the controller 430 may adaptively change the output speed such that the tactile feedback is output at a speed different from the reference speed. Also, the controller 430 may predict the moving speed of the user, and control the output speed of the tactile feedback based on the predicted moving speed.

The controller 430 may adaptively change the output speed of the tactile feedback based on a change in the exercise intensity information. For example, when the exercise intensity information is in the range less than the target range, the output speed of the tactile feedback may be increased when compared to the reference speed. When the exercise intensity information is in the range less than the target range despite the outputting of the tactile feedback, the controller 430 may sense that the exercise intensity information is not changing in a desiring direction. The controller 430 may increase the output speed of the tactile feedback based on a result of the sensing.

The exercise feedback provision apparatus 400 may further include a user interface configured to receive, from the user, an input for setting the output speed. For example, the exercise feedback provision apparatus 400 may further include a touch display. In response to a touch input of the user on the touch display, the exercise feedback provision apparatus 400 may set the output speed of the tactile feedback.

The exercise feedback provision apparatus 400 may further include a communication interface configured to receive the output speed from an external device. The external device may be a wearable device and/or a mobile terminal paired with the exercise feedback provision apparatus 400. The external device may be a device included in an identical network, for example, a wireless body area network (WBAN), to the exercise feedback provision apparatus 400. The user may set the output speed of the tactile feedback, using the external device. The external device may transmit the set output speed to the exercise feedback provision apparatus 400.

Since the descriptions provided with reference to FIGS. 1 through 3 are also applicable to FIG. 4, repeated descriptions will be omitted for increased clarity and conciseness.

Figure 5:
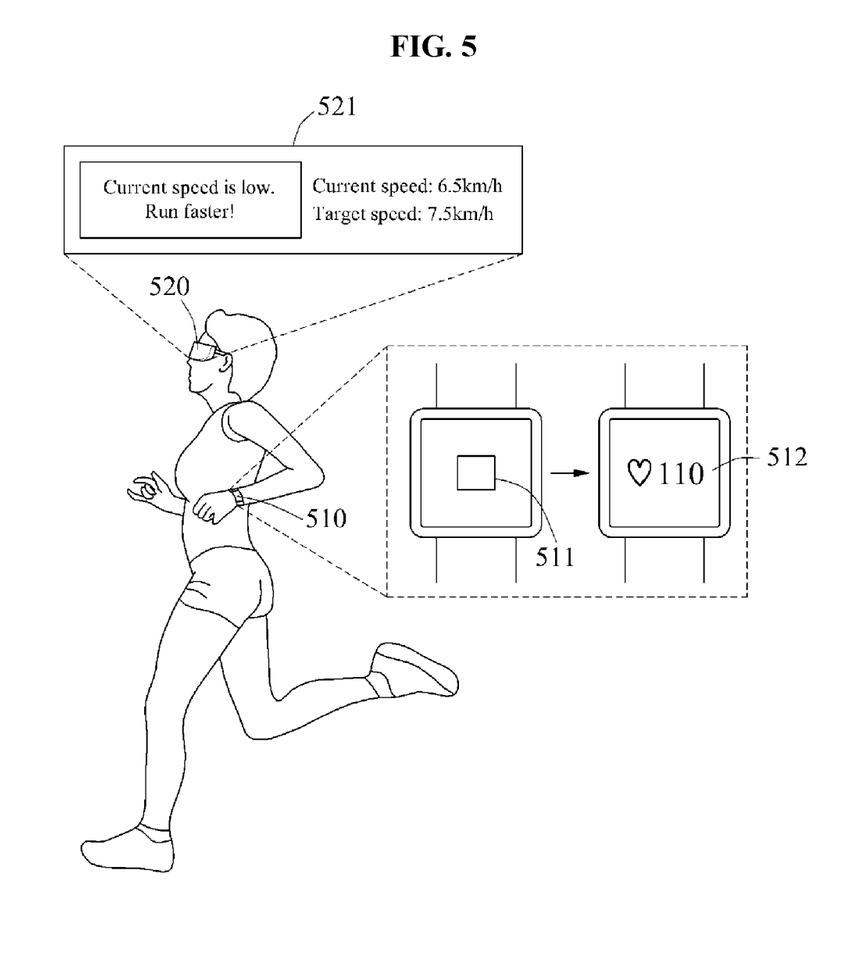
FIGS. 5 and 6 are diagrams illustrating examples of operating an exercise feedback provision apparatus.

FIGS. 5 and 6 are diagrams illustrating examples of operating an exercise feedback provision apparatus. Referring to FIG. 5, a user wears wearable devices 510 and 520 while exercising. The wearable devices 510 and 520 provide an exercise feedback to the user.

The wearable device 510 includes a sensor 511 that measures a heart rate of the user, and a display 512 that displays the heart rate of the user. Also, the wearable device 510 may include a vibration motor to provide a tactile feedback to the user.

The wearable device 510 measures the heart rate of the user as "110". A range of a target heart rate that corresponds to an optimal exercise intensity of the user may be between "120" and "140". Since the heart rate of the user is less than the range of the target heart rate, the wearable device 510 may provide the tactile feedback based on an output pattern corresponding to the heart rate. The user may recognize the output pattern of the tactile feedback, and increase a running speed. The wearable device 510 may sense whether the heart rate of the user reaches the range of the target heart rate. Based on a result of the sensing, the wearable device 510 may suspend the tactile feedback. The user may increase the running speed until the tactile feedback is suspended.

The wearable device 520 outputs a message 521 indicating the user is to increase the running speed. The wearable device 520 displays a current running speed, and a target running speed corresponding to the optimal exercise intensity of the user.

Figure 6:
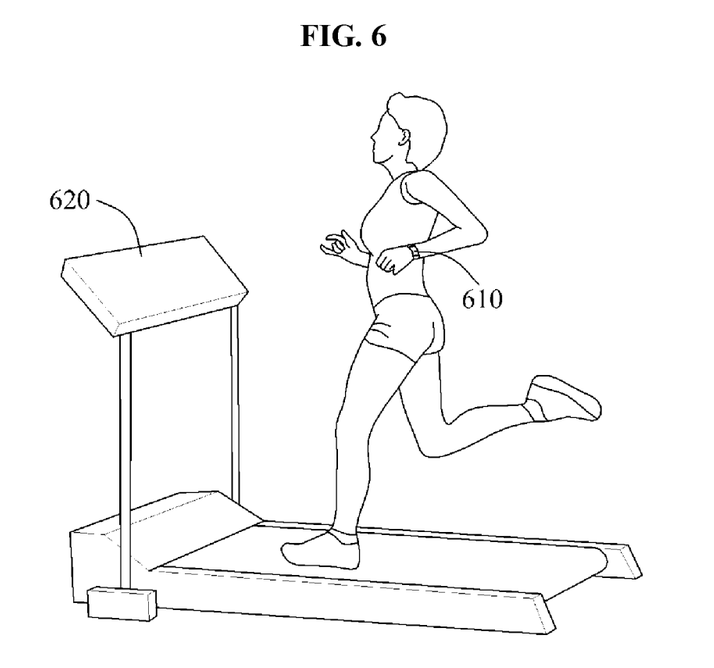

Referring to FIG. 6, a user wears a wearable device 610 while exercising and using a health device 620. The wearable device 610 may be connected with the health device 620 through a wired network and/or a wireless network.

The wearable device 610 may verify whether a running speed of the user is in a target speed range. When the running speed of the user is in a range less than the target speed range, the wearable device 610 may provide a first tactile feedback to the user. The wearable device 610 may transmit a message to the health device 620 to increase the running speed. When the running speed of the user is in a range greater than the target speed range, the wearable device 610 may provide a second tactile feedback to the user. The wearable device 620 may transmit a message to the health device 620 to reduce the running speed.

Figure 7:
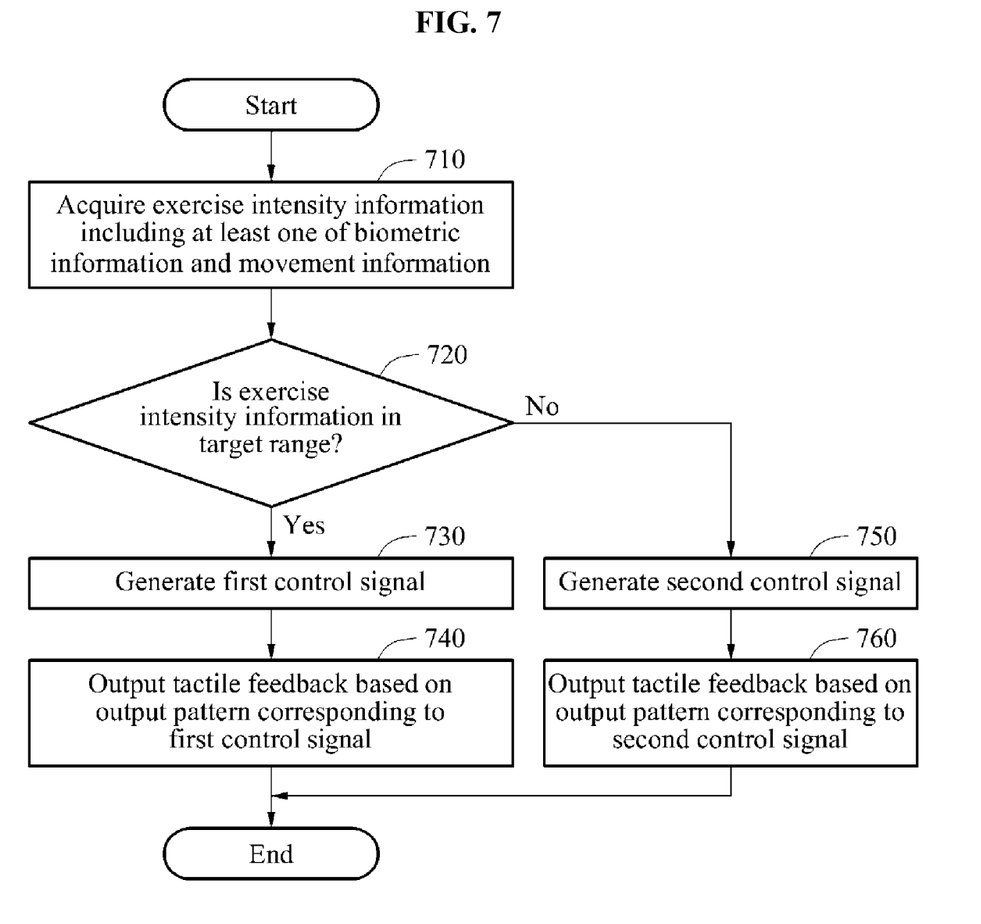
FIG. 7 is a flowchart illustrating an example of an exercise feedback provision method.

FIG. 7 is a flowchart illustrating an example of an exercise feedback provision method. The exercise feedback provision method is performed by an exercise feedback provision apparatus.

In operation 710, the exercise feedback provision apparatus acquires exercise intensity information including at least one of user biometric information and user movement information.

In operation 720, the exercise feedback provision apparatus verifies whether the exercise intensity information is in a target range. The exercise feedback provision apparatus may generate a control signal corresponding to a result of the verifying. When the exercise intensity information is verified to be in the target range, the exercise feedback provision apparatus continues in operation 730. Otherwise, the exercise feedback provision apparatus continues in operation 750.

In operation 730, the exercise feedback provision apparatus generates a first control signal.

In operation 740, the exercise feedback provision apparatus outputs a tactile feedback based on an output pattern corresponding to the first control signal.

In operation 750, the exercise feedback provision apparatus generates a second control signal.

In operation 760, the exercise feedback provision apparatus outputs a tactile feedback based on an output pattern corresponding to the second control signal.

As another example, the exercise feedback provision apparatus may output the tactile feedback based on the output pattern corresponding to the first control signal when the exercise intensity information is in a range greater than the target range. The exercise feedback provision apparatus may output the tactile feedback based on the output pattern corresponding to the second control signal when the exercise intensity information is in the target range. In this example, the output pattern corresponding to the second control signal may be a pattern in which the tactile feedback is not output. The exercise feedback provision apparatus may output a tactile feedback based on a third output pattern corresponding to a third control signal when the exercise intensity information is in a range less than the target range.

The exercise feedback provision apparatus may receive an output pattern from an external device, using a communication interface. Also, the exercise feedback provision apparatus may receive, from a user, a selection input for setting the output pattern.

Since the descriptions provided with reference to FIGS. 1 through 6 are also applicable to FIG. 7, repeated descriptions will be omitted for increased clarity and conciseness.

Figure 8:
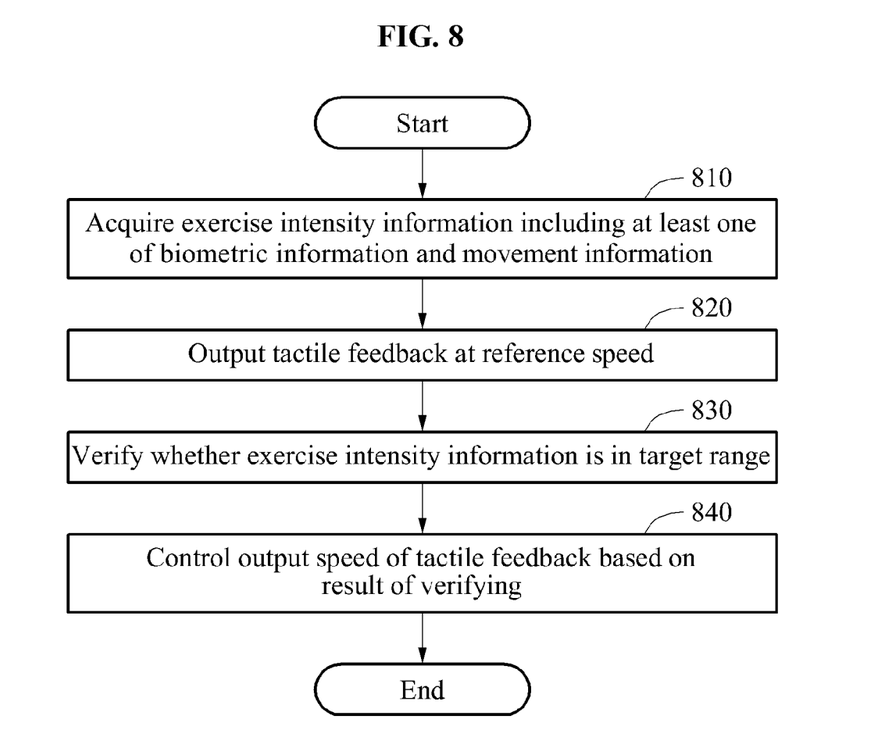
FIG. 8 is a flowchart illustrating another example of an exercise feedback provision method.

FIG. 8 is a flowchart illustrating another example of an exercise feedback provision method. The exercise feedback provision method is performed by an exercise feedback provision apparatus.

In operation 810, the exercise feedback provision apparatus acquires exercise intensity information including at least one of user biometric information and user movement information.

In operation 820, the exercise feedback provision apparatus outputs a tactile feedback at a reference speed.

In operation 830, the exercise feedback provision apparatus verifies whether the exercise intensity information is in a target range.

In operation 840, the exercise feedback provision apparatus controls an output speed of the tactile feedback based on a result of the verifying.

Since the descriptions provided with reference to FIGS. 1 through 6 are also applicable to FIG. 8, repeated descriptions will be omitted for increased clarity and conciseness.

The various modules, elements, and methods described above may be implemented using one or more hardware components, or a combination of one or more hardware components and one or more software components.

A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

As a non-exhaustive illustration only, a terminal or device described herein may be a mobile device, such as a cellular phone, a personal digital assistant (PDA), a digital camera, a portable game console, an MP3 player, a portable/personal multimedia player (PMP), a handheld e-book, a portable laptop PC, a global positioning system (GPS) navigation device, a tablet, a sensor, or a stationary device, such as a desktop PC, a high-definition television (HDTV), a DVD player, a Blue-ray player, a set-top box, a home appliance, or any other device known to one of ordinary skill in the art that is capable of wireless communication and/or network communication.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An exercise feedback provision method of a wearable device, the method comprising:
   acquiring exercise intensity information of a user wearing the wearable device;
   determining whether the exercise intensity information is greater than a target set on the wearable device or less than the target; and
   outputting a first tactile feedback based on a first vibration pattern in response to the exercise intensity information being determined to be greater than the target, and
   outputting a second tactile feedback based on a second vibration pattern, different from the first vibration pattern, in response to the exercise intensity information being determined to be less than the target.

2. The method of claim 1, wherein the exercise intensity information and the target are each in units of time and distance.

3. The method of claim 1, wherein the exercise intensity information comprises user movement information.

4. The method of claim 1, wherein the exercise intensity information comprises at least one of moving distance information, moving speed information, and step count information.

5. The method of claim 1, wherein the first tactile feedback is a guidance to guide the user to change the exercise intensity information to reflect a decrease in a moving speed of the user, and the second tactile feedback is a guidance to guide the user to change the current exercise intensity information to reflect an increase in the moving speed of the user.

6. The method of claim 1, further comprising:
   displaying at least one of information corresponding to the target and the exercise intensity information.

7. The method of claim 1, further comprising:
   displaying a first state information when the exercise intensity information is greater than the target and displaying a second state information when the exercise intensity information is less than the target.

8. The method of claim 1, further comprising:
   displaying information indicating whether the exercise intensity information is less than the target.

9. The method of claim 1, wherein an output speed of the first tactile feedback is different from an output speed of the second tactile feedback.

10. The method of claim 1, wherein an output period of the first tactile feedback is different from an output period of the second tactile feedback.

11. An exercise feedback provision method of a wearable device, the method comprising:
    acquiring exercise intensity information of a user wearing the wearable device;
    determining whether the exercise intensity information is within a first range set on the wearable device or a second range set on the wearable device; and
    outputting a first tactile feedback based on a first vibration pattern in response to the exercise intensity information being determined to be within the first range, and
    outputting a second tactile feedback based on a second vibration pattern different from the first vibration pattern in response to the exercise intensity information being determined to be within the second range.

12. The method of claim 11, wherein the exercise intensity information is in units of time and distance.

13. The method of claim 11, wherein the exercise intensity information comprises user movement information.

14. The method of claim 11, wherein the exercise intensity information comprises at least one of moving distance information, moving speed information, and step count information.

15. The method of claim 11, wherein the first tactile feedback is a guidance to guide the user to change the exercise intensity information to reflect a decrease in a moving speed of the user, and the second tactile feedback is a guidance to guide the user to change the current exercise intensity information to reflect an increase in the moving speed of the user.

16. The method of claim 11, further comprising:
    displaying a first state information when the exercise intensity information is within the first range and displaying a second state information when the exercise intensity information is within the second range.

17. The method of claim 11, further comprising:
    displaying information indicating whether the exercise intensity information is within the first range or the second range.

18. The method of claim 11, wherein an output speed of the first tactile feedback is different from an output speed of the second tactile feedback.

19. The method of claim 11, wherein an output period of the first tactile feedback is different from an output period of the second tactile feedback.

* * * * *